United States Patent
Patel et al.

(10) Patent No.: US 9,363,725 B2
(45) Date of Patent: Jun. 7, 2016

(54) TECHNIQUES FOR DYNAMICALLY SWITCHING BETWEEN SYNCHRONOUS AND ASYNCHRONOUS OPERATION MODES IN BODY AREA NETWORKS

(75) Inventors: Maulin D. Patel, Tuckahoe, NY (US); Richard Chen, Croton-On-Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 469 days.

(21) Appl. No.: 13/058,010

(22) PCT Filed: Aug. 7, 2009

(86) PCT No.: PCT/IB2009/053494
§ 371 (c)(1),
(2), (4) Date: Apr. 6, 2011

(87) PCT Pub. No.: WO2010/018518
PCT Pub. Date: Feb. 18, 2010

(65) Prior Publication Data
US 2011/0176503 A1    Jul. 21, 2011

Related U.S. Application Data

(60) Provisional application No. 61/087,751, filed on Aug. 11, 2008.

(51) Int. Cl.
*H04W 36/14* (2009.01)
*H04W 84/10* (2009.01)
(Continued)

(52) U.S. Cl.
CPC .............. *H04W 36/14* (2013.01); *A61B 5/0022* (2013.01); *A61B 5/0024* (2013.01); *A61B 2560/0209* (2013.01); *H04W 84/10* (2013.01); *H04W 88/06* (2013.01)

(58) Field of Classification Search
CPC ..... H04W 36/14; H04W 84/10; H04W 88/06; A61B 2560/0209; A61B 5/0024; A61B 5/0022

USPC ................... 370/235, 311, 329, 349; 455/502
See application file for complete search history.

(56) References Cited

U.S. PATENT DOCUMENTS

2002/0160785 A1   10/2002  Ovesjo
2005/0037758 A1    2/2005  Rimoni
(Continued)

FOREIGN PATENT DOCUMENTS

CN          1630216 A       6/2005
CN          1981458 A       6/2007
(Continued)

OTHER PUBLICATIONS

Wei Ye et al., "Medium Access Control with Coordinated Adaptive Sleeping for Wireless Sensor Networks" IEEE/ACM Transactions on Networking, vol. 12, No. 3, Jun. 2004, pp. 493-506.
(Continued)

*Primary Examiner* — Pao Sinkantarakorn
*Assistant Examiner* — Richard Chang
(74) *Attorney, Agent, or Firm* — Larry Liberchuk (57) ABSTRACT

Techniques for dynamically switching between synchronous and asynchronous operation modes in body area networks (BANs). One embodiment includes a method (400) for transitioning from an asynchronous mode to a synchronous mode in a medium access control (MAC) of a BAN. A device receiving a switch mode command (S410) performs the acts comprising: setting a timer to a time period specified in the switch mode command (S430); propagating the received switch mode command to other devices in the BAN (S440); upon expiration of the time period, tuning to a channel selected from a set of channels reserved for the synchronous mode (S460); and initializing a device to operate as either a master device or a slave device in the synchronous mode of operation (S470). Another embodiment includes a method (300) for transitioning from a synchronous mode to an asynchronous mode in a MAC of a body area networks (BAN).

17 Claims, 4 Drawing Sheets

(51) Int. Cl.
    *H04W 88/06*    (2009.01)
    *A61B 5/00*    (2006.01)

(56) References Cited

U.S. PATENT DOCUMENTS

| | | | |
|---|---|---|---|
| 2006/0166699 | A1 | 7/2006 | Aghvami |
| 2007/0159321 | A1 | 7/2007 | Ogata |
| 2007/0253021 | A1 | 11/2007 | Mehta |
| 2007/0258395 | A1* | 11/2007 | Jollota et al. .............. 370/310 |
| 2007/0280160 | A1* | 12/2007 | Kim et al. .............. 370/331 |
| 2008/0188225 | A1 | 8/2008 | Park |
| 2009/0103437 | A1* | 4/2009 | Kim et al. .............. 370/235 |
| 2010/0272095 | A1* | 10/2010 | Alberti et al. .............. 370/350 |

FOREIGN PATENT DOCUMENTS

| | | |
|---|---|---|
| CN | 101053181 A | 10/2007 |
| JP | 2008054798 A | 3/2008 |
| WO | WO2005022846 A1 | 3/2005 |
| WO | WO2006092769 A1 | 9/2006 |
| WO | WO2008044089 A1 | 4/2008 |
| WO | WO2008055135 A2 | 5/2008 |

OTHER PUBLICATIONS

Tijs Van Dam et al., "An Adaptive EnergyEfficient MAC Protocol for Wireless Sensor Networks", in the Proceedings of ACM SenSys, Nov. 2003, Los Angeles.

Peng Lin et al., "Medium Access Control With a Dynamic Duty Cycle for Sensor Networks", Proceedings of the IEEE WCNC 2004, pp. 1534-1539.

El-Hoiydi et al., "WiseMAC: An Ultra Low Power MAC Protocol for the Downlink of Infrastructure Wireless Sensor Networks" Published in the Proceedings of the Ninth IEEE Symposium on Computers and Communication, ISCC'04, pp. 244-251, Alexandria, Egypt, Jun. 2004.

Joseph Polastre et al.,"Versatile Low Power Media Access for Wireless Sensor Networks", ACM SenSys, Nov. 2004, pp. 95-107.

Buettner et al., "X-MAC: A Short Preamble MAC Protocol for Duty-Cycled Wireless Sensor Networks" ACM SenSys 2006.

Klues, K. et al, "Link Layer Support for Unified Radio Power", Washington University Open Scholarship, Department of Computer Science & Engineering, Report Number: 2006-63, Jan. 1, 2006.

Jian Q. Rt Al, "Overview of MAC Protocols in Wireless Sensor Networks", Journal of Software, vol. 19, No. 2, Feb. 2008, pp. 389-403.

* cited by examiner

TECHNIQUES FOR DYNAMICALLY SWITCHING BETWEEN SYNCHRONOUS AND ASYNCHRONOUS OPERATION MODES IN BODY AREA NETWORKS

This application claims the benefit of U.S. Provisional Application No. 61/087,751 filed on August 11.

The invention generally relates to techniques to switch operation modes in body area networks (BANs).

A body area network (BAN) is primarily designed for permanent monitoring and logging of vital signs. An exemplary BAN, shown in FIG. 1, includes multiple slave devices 120 which are typically sensors that can be either wearable or implanted into the human body. The slave devices 120 monitor vital body parameters and movements, and communicate with each other over a wireless medium. The slave devices 120 can transmit data from a body to one or more master devices 130 from where the data can be forwarded, in real-time, to a hospital, clinic or elsewhere over a local area network (LAN), a wide area network (WAN), a cellular network, and the like.

Figure 1:
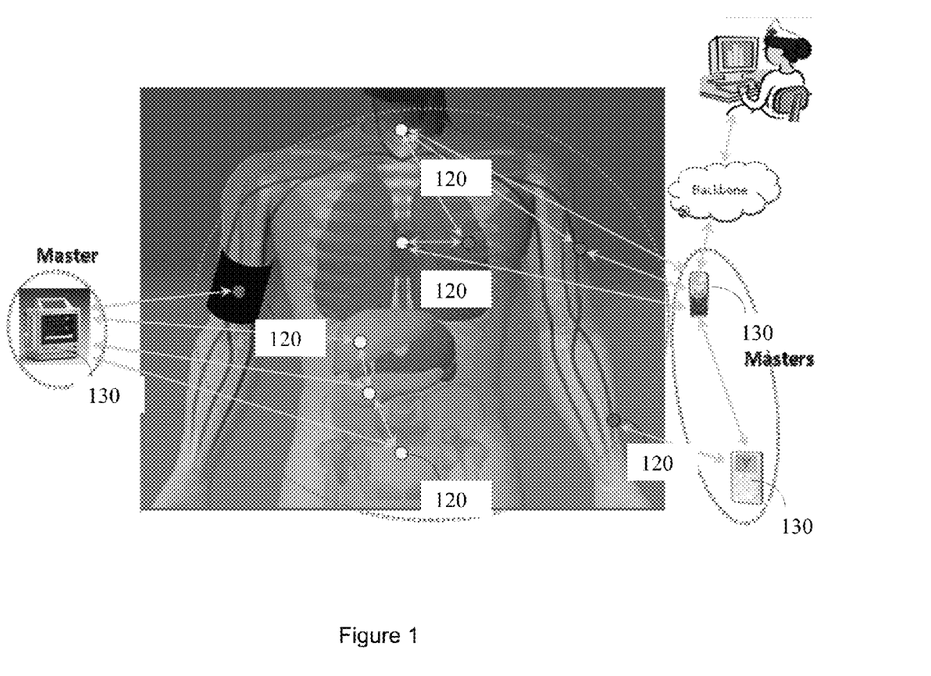
FIG. 1 is a schematic diagram of a body area wireless network.

One of the important factors in designing a BAN is the energy efficiency of slave devices 120 and/or master devices 130. Efficient energy consumption can be achieved by optimally duty cycling a receiver device (i.e., a device receiving data) between a listen state and a sleep state. The radio of a device is turned off when the device neither transmits nor receives data, thereby reducing the energy consumption of the device. A duty cycling is performed by a medium access control (MAC) protocol with the aim of minimizing idle listening, overhearing times, collisions of data transmissions and controlling overhead, which ultimately leads to power savings.

In the related art, several synchronous and asynchronous MAC duty cycling techniques are disclosed. A synchronous duty cycling includes periodically advertising sleep and wake-up schedules, and synchronizing awake times of receiver devices. This requires an explicit synchronization mechanism, such as beacons, to synchronize clocks and advertise schedules. MAC protocols, for example, SMAC, TMAC and DSMAC, and the like employ explicit synchronization mechanisms to synchronize their active times. The SMAC protocol is disclosed in "Medium Access Control with Coordinated Adaptive Sleeping for Wireless Sensor Networks" by Wei Ye, John Heidemann and Deborah Estrin in IEEE/ACM Transactions on Networking, Vol. 12, No. 3, June 2004, pp 493-506. The TMAC protocol is described by Tijs van Dam and Koen Langendoen in "An Adaptive Energy Efficient MAC Protocol for Wireless Sensor Networks" in the Proceedings of ACM SenSys, November 2003, Los Angeles. The DSMAC is discussed by Peng Lin, Chunming Qiao and Xin Wang in "Medium Access Control With A Dynamic Duty Cycle For Sensor Networks" in the Proceedings of the IEEE WCNC 2004, pp. 1534-1539.

In a synchronous duty cycling MAC protocol, the active times of devices are synchronized, whereby the broadcasting and multicasting of data is simple and efficient. This technique is also suitable for medium reservation, mobility support and co-existence support. Accordingly, synchronous mechanisms are inherently suitable to guarantee quality of service (QoS) support. However, periodic synchronization incurs high overhead, which increases the energy consumption. In addition, sender devices (i.e., devices sending data) typically try to send their packets during a globally synchronized active time, such that the probability of collision increases. If a potential sender device loses the contention, the next opportunity arrives during the next active time. Moreover, in a multi-hop communication, after a forwarding device (a device on the path between a source and destination device) receives a data packet, it must wait until the next active time arrives before attempting to transmit that packet. Thus, per hop the latency in a synchronous duty cycling technique is relatively high.

In an asynchronous duty cycling, a sender device and a listener device (i.e., a device that listens to the medium) have independent sleep and awake times, whereby an explicit synchronization mechanism is not required. A preamble sampling technique is widely used in asynchronous duty cycling MAC protocols, such as WiseMAC, B-MAC and X-MAC. The WiseMAC is further described in "*WiseMAC: An Ultra Low Power MAC Protocol for the Downlink of Infrastructure Wireless Sensor Networks*" by El-Hoiydi, et al. published in the Proceedings of the Ninth IEEE Symposium on Computers and Communication, ISCC'04, pages 244-251, Alexandria, Egypt, June 2004. The B-MAC is described in "*Versatile Low Power Media Access for Wireless Sensor Networks*", ACM SenSys November 2004 by Polastre, et al., and the X-MAC protocol is published in "*X-MAC: A Short Preamble MAC Protocol for Duty-Cycled Wireless Sensor Networks*" ACM SenSys 2006, by Buettner, et al.

Figure 2:
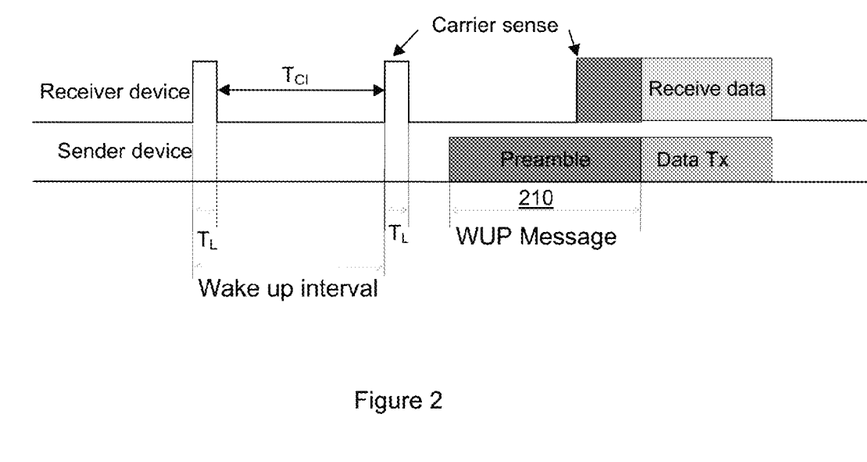
FIG. 2 is a diagram for illustrating the operation of asynchronous duty cycling technique.

As illustrated in FIG. 2, in the preamble sampling technique all the devices periodically listen to the medium for a short duration of time "$T_L$" and then return to a sleep state for the duration of a time "$T_{CI}$", if the medium is idle. The time $T_{CI}$—between two successive listen times $T_L$—is a check interval. The combination of time intervals $T_{CI}$ and $T_L$ is a wake-up time interval. When a sender device has data to deliver, it transmits a wake-up (WUP) message 210 that is longer than the check time interval $T_{CI}$, of a receiver device. In the preamble sampling technique a WUP message 210 carries only preambles and does not carry any other information. When a receiver device wakes-up, it senses the medium and detects the WUP message 210. This forces the receiver device to stay awake until the data is fully received and/or the medium becomes idle again.

The length of the WUP message 210 must be longer than the check interval $T_{CI}$ to ensure that a receiver device is awake when actual data is transmitted. If a check interval $T_{CI}$ of a receiver device is very long, then WUP message transmissions can occupy the medium for a very long time, thereby preventing other devices from accessing the medium.

The main advantage of an asynchronous duty cycling is its simplicity, as there is no synchronization overhead which may result in improved energy efficiency. Devices can update their wake up schedules independently. In low duty cycle networks, the snoop time intervals of devices are distributed in time which reduces the probability of collision and latency. A snoop time interval is the minimum duration during which all the devices must listen to the medium after they wake up. However, broadcast/multicast is inefficient in the asynchronous mode and, in addition, medium reservations cannot be supported. As a result, the QoS that can be provided and guaranteed in such an operation mode is limited.

As can be realized from the above discussion the asynchronous and synchronous duty cycling techniques independently achieve optimal performance in certain scenarios. Therefore, it would be desirable to provide a solution that could improve the performance of the BAN by dynamically switching between these different techniques as deemed suitable by the application.

Certain embodiments of the invention include a method for transitioning from a synchronous mode to an asynchronous mode in a medium access control (MAC) of a body area networks (BAN). The method comprises receiving, by each device, a switch mode command that causes: setting a timer to a time period specified in the switch mode command; upon expiration of the time period, tuning the device to a channel selected from a set of channels reserved for the asynchronous mode; and causing the device to operate in the asynchronous mode over the reserved channel.

Certain embodiments of the invention also include a method for transitioning from an asynchronous mode to a synchronous mode in a medium access control (MAC) of a body area network (BAN). The method comprises receiving, by each device, a switch mode command that causes: setting a timer to a time period specified in the switch mode command; propagating the received switch mode command to other devices in the BAN; upon expiration of the time period, tuning to a channel selected from a set of channels reserved for the synchronous mode; and initializing a device to operate as either a master device or a slave device in the synchronous mode of operation.

The subject matter that is regarded as the invention is particularly pointed out and distinctly claimed in the claims at the conclusion of the specification. The foregoing and other features and advantages of the invention will be apparent from the following detailed description taken in conjunction with the accompanying drawings.

It is important to note that the embodiments disclosed by the invention are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views.

The asynchronous and synchronous duty cycling techniques utilized by the MAC protocol are also referred to as operation modes of the BAN. Thus, the synchronous and asynchronous MAC duty cycling techniques will be referred to as synchronous and asynchronous modes, respectively.

Applications executed in a BAN can switch between synchronous and asynchronous modes to benefit from the advantages of each mode according to the requirements of the application. This is important in BANs, as such networks are intended to support a wide range of applications which have diverse sets of requirements. For example, devices may switch to a synchronous mode when guaranteed QoS is a requirement of the application, and then switch back to an asynchronous mode for an ultra-low power operation. Consider a typical BAN scenario in which a wearable master device manages a few implanted slave devices. When a patient takes a shower, the master device may not be in direct communication range with the implanted slave devices. In this scenario, an asynchronous mode can be used to provide the basic communication capabilities among the implanted devices. Asynchronous mode can also be used as a wake-up or a start-up mechanism. Once the devices are awake and the network is formed, the devices may switch to the synchronous mode. As another example, devices may switch to the asynchronous mode when a master device battery is critically low or a master device disappears, and no other device can play the role of the master.

The techniques for dynamically switching between modes, as disclosed in accordance with certain embodiments of the invention, are performed by a MAC protocol that provides the hooks for scheduling and coordinating the mode transition, where the decision to trigger a mode switch is performed by a higher layer of a communication protocol (e.g., the application layer). As disclosed below, switching from one mode to another often requires tuning the radio to a different channel or channels in order to prevent devices operating in synchronous and asynchronous modes from coexisting on the same channel. With this aim, frequency bands or channels are grouped into two sets: one set restricted to devices operating in the synchronous mode, and the other set is restricted to devices operating in the asynchronous mode. These two sets are mutually disjoint.

Figure 3:
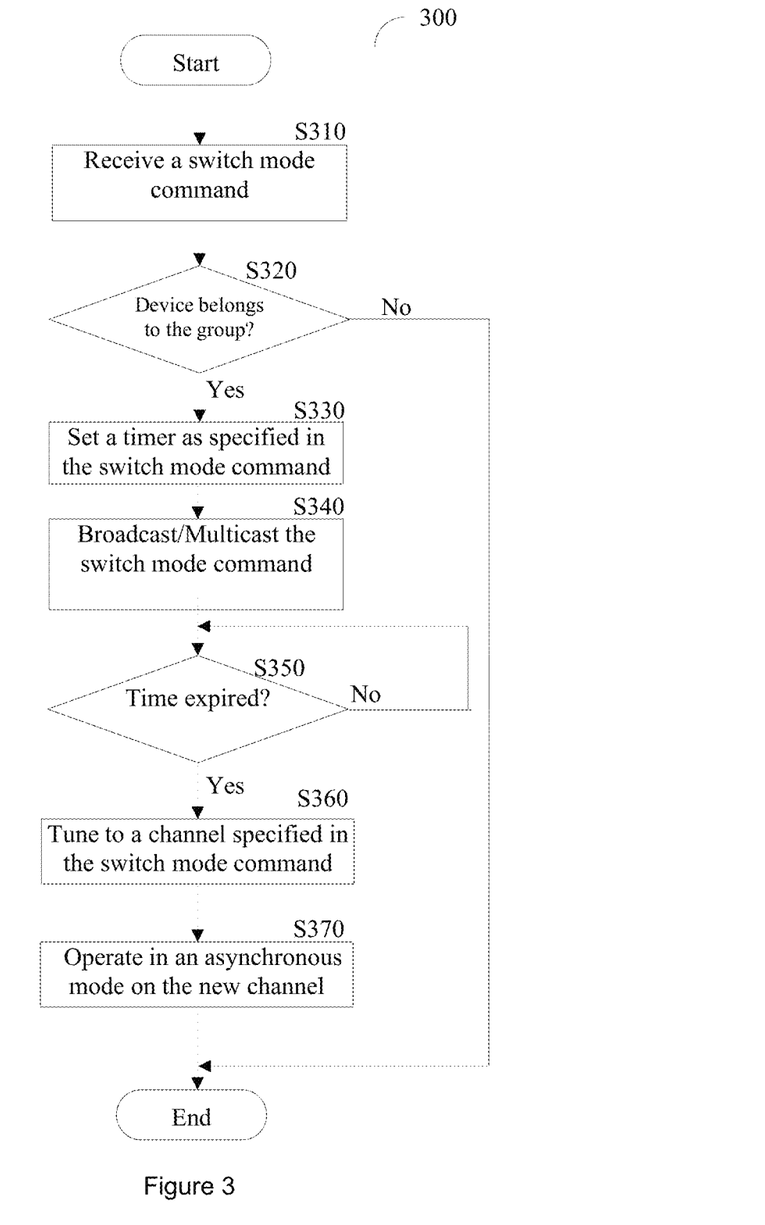
FIG. 3 is a flowchart for describing the method for transitioning from a synchronous mode to an asynchronous mode implemented in accordance with one embodiment of the invention.

FIG. 3 shows an exemplary and non-limiting flowchart 300 for describing the method for transitioning from a synchronous mode to an asynchronous mode implemented in accordance with one embodiment of the invention. A BAN typically includes two types of devices: masters and slaves. In a preferred embodiment, a master device communicates with a set of its slave devices using local beacons, while master devices can communicate with each other using global beacons.

At S310 a device receives a switch mode command from a peer device or from a higher layer. The switch mode command may include, for example, a time when the new mode becomes effective, the channel (frequency band) that should be used for the asynchronous mode of operation, and the identity of the group/subgroup of devices that should switch the mode. In one embodiment, the value of time can be specified as an offset of time from the current time when the mode switch should be executed.

At S320 the device receiving the command checks whether it belongs to the group identified in the switch mode command, and if so execution continues with S330; otherwise, execution ends as the device is not required to change its mode. That is, devices which do not belong to the group identified in the switch mode command continue their synchronous mode of operation on the same channel.

At S330 each device that received the switch mode command and intends to switch to the asynchronous mode sets up a timer to the amount of time specified in switch mode command. The purpose of delaying the mode switching is to allow sufficient time for the switch mode command to propagate through the entire network and to prepare for the mode switching. The value of the offset of the time specified in the switch mode command is updated as the command propagates to reflect the exact time when the new mode becomes effective. When the specified time is elapsed, the devices receiving the command and intending to switch to asynchronous mode simultaneously switch to the asynchronous mode of operation, thereby minimizing the disruption of service.

Optionally, at S340 the master device broadcasts or multicasts the switch mode command in a global beacon to coordinate the change in the mode of operation with peer master devices, i.e., master devices connected with each other in a peer-to-peer connection. Each master device receiving the switch mode command from a peer device or a higher layer and intending to switch to the asynchronous mode may inform its slave devices about an upcoming mode change via a switch mode command sent in its local beacons.

At S350 it is checked if the time period measured by the timer has expired, and if so execution continues to S360; otherwise, execution waits at S350. At S360 each device is tuned to a channel identified in the switch mode command (i.e., one of the channels in the set of asynchronous channels), and thereafter at S370 the devices start performing their routine tasks in the asynchronous mode.

In accordance with an embodiment of the invention, these tasks include sending a wake-up (WUP) message from a sender device to one or more target receiver devices when a wireless medium of the BAN is free; determining if at least one target receiver device responds with a READY message during a sniff time interval of the sender device; determining if a number of WUP messages transmitted by the sender device exceeds a predefined threshold, when the READY message was not received; and setting the sender device to operate in a TURN mode when the number of WUP messages exceeds the predefined threshold. This mode of operation is described in greater detail in a co-pending application entitled "Duty Cycling Techniques in Medium Access Control (MAC) Protocols for Body Area Networks." A sniff time interval is a fixed duration of time after transmitting a WUP message, during which a sender device listens to the medium.

It should be noted that during operation of the BAN one or more slave devices may not receive the switch mode command from their master(s), and/or one or more master devices may silently disappear. This may, for example, be due to interference/collisions on the channel or failure of the master device. To handle such situations slave devices that have not received beacons from their master device for a predefined period of time scan the channel to detect beacons from another master device to whom they can join. If the slave devices do not find a master device to which they can join within the predefined period of time, then slave devices conclude that the master device has disappeared and they transition to an asynchronous mode of operation. In this case, all the slave devices transition to a default (prearranged) channel to avoid ambiguity.

Figure 4:
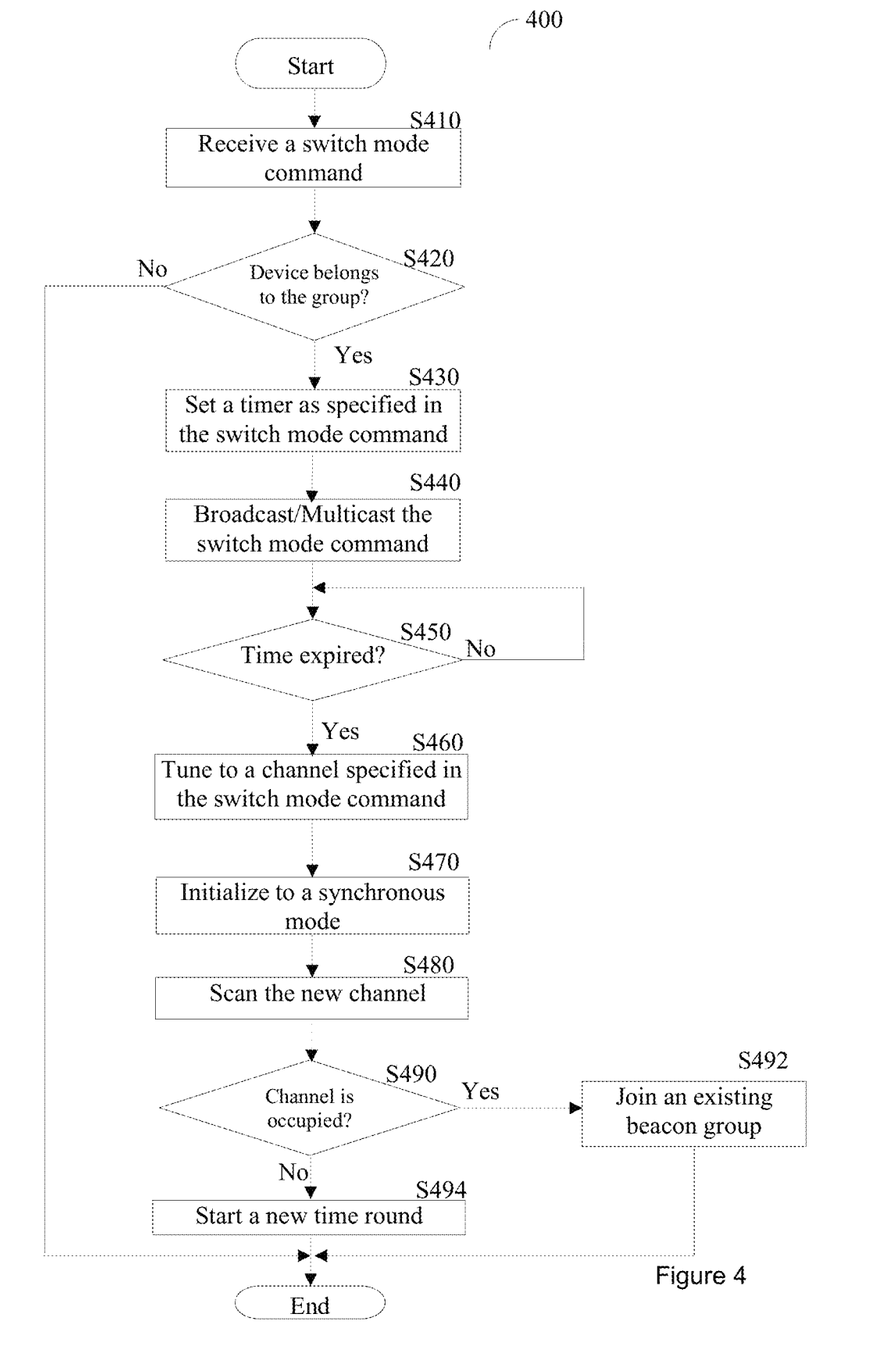
FIG. 4 is a flowchart for describing the method for transitioning from an asynchronous mode to a synchronous mode implemented in accordance with one embodiment of the invention.

FIG. 4 shows an exemplary and non-limiting flowchart 400 for describing the method for transitioning from an asynchronous mode to a synchronous mode implemented in accordance with one embodiment of the invention.

At S410 a device receives a switch mode command from a peer device or from a higher layer (e.g., an application layer). The command may include, for example, a future time when the new mode becomes effective, the channel identified for the synchronous mode of operation (among the channels reserved for the synchronous mode of operation), and the identities of the group of devices to whom the switch mode command is intended. In one embodiment of the invention, the value of time can be specified as an offset of time from the current time when the mode switch should be performed.

At S420, a device receiving the command checks whether it belongs to the group identified in the switch mode command, and if so execution continues at S430; otherwise, execution terminates as the device is not required to switch its mode of operation. That is, devices which do not belong to the group identified in the switch mode command continue their operation in the asynchronous mode on the same channel.

At S430 each device intending to switch to the synchronous mode sets up a timer to the amount of time specified in the received switch mode command. The purpose of delaying the switching mode is to allow sufficient time for the switch mode command to propagate through the entire network and to prepare for mode switching. The value of the offset of time specified in the outgoing switch mode command is updated to reflect the exact time when the mode switch is to be executed. When the specified time has elapsed, devices intending to switch their modes simultaneously switch to the synchronous mode of operation, thereby minimizing the disruption of service.

At S440, the device receiving the switch mode command may broadcast or multicast the switch mode command to coordinate the change in the mode of operation with its peer devices, i.e., devices connected with each other in a peer-to-peer connection. At S450 it is checked if the time measured by the timer has expired, and if so execution continues with S460; otherwise, execution waits at S450.

At S460, each device ready to switch the mode is tuned to the channel identified in the switch mode command, i.e., one of the channels in the set of synchronous mode channels. At S470, the devices are initialized to their predefined roles (e.g. master or slave) as implemented in the synchronous mode of operation of the MAC protocol. At S480, each master device scans the new channel to determine if the channel is occupied by other master devices. That is, each transitioning master device checks for other global beacons in the channel that is now tuned to. At S490 it is checked if the channel is occupied by other master devices, and if so, at S492 transitioning master devices join the existing beacon group and start transmitting their global and local beacons; otherwise, the channel is vacant, and at S494 the transitioning master device starts a new time round and transmits its global beacons. The master devices that transition subsequently will find the channel occupied and join the first master at S492.

In a preferred embodiment of the invention the access to the medium is divided into fixed and repeated duration time rounds, where a time round is a data structure designed to include a predefined number of superframes each of which includes a fixed number of time slots.

It should be noted that when a slave device switches the mode, it scans the channel to detect local beacons of master devices to which the slave device can join. Once such a master device is detected, the slave device joins this master device and continues tracking its local beacons.

As stated above during the operation of the BAN one or more devices may not receive the switch mode command due to message collisions or interference on the channel, whereby these devices will not switch to the synchronous mode. To prevent this failure, the master device verifies whether all of its neighbor devices have switched to the synchronous mode. If one or more neighbor devices have not transitioned, then during its idle time the master device switches back to the asynchronous mode (for the duration of the idle time) to rebroadcast or re-multicast the switch mode command.

The principles of the invention may be implemented as hardware, firmware, software or any combination thereof. Moreover, the software is preferably implemented as an application program tangibly embodied on a program storage unit or computer readable medium. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The invention claimed is:

1. A method for transitioning from a synchronous mode to an asynchronous mode in a medium access control (MAC) of a body area network (BAN) upon receiving a switch mode command, comprising:
setting a timer to a time period specified in the switch mode command for switching from the synchronous mode to the asynchronous mode within the BAN;
upon expiration of the time period, tuning a device to a channel selected from a first set of channels in the BAN reserved for the asynchronous mode, wherein the first set of channels is different from a second set of channels that is reserved for the synchronous mode in the BAN; and
causing the device to operate in the asynchronous mode over the reserved channel, wherein the device is configured for asynchronously duty cycling between sleep and wakeup times.

2. The method of claim 1, further comprising receiving the switch mode command at the device and propagating the received switch mode command to other devices in the BAN.

3. The method of claim 1, wherein the switch mode command includes at least a time when a mode switch is to be performed, the channel for the asynchronous mode of operation, and identity of a group of devices that should switch their mode.

4. The method of claim 2, wherein the switch mode command is sent from either a peer device or an application layer.

5. The method of claim 4, further comprising checking by the device receiving the switch mode command if the device belongs to the group of devices designated in the switch mode command.

6. The method of claim 1, further comprising tuning each slave device operating in the asynchronous mode to a prearranged channel being selected from the first set of asynchronous mode channels, when the slave device cannot communicate with a master device for a predefined duration of time.

7. A non-transitory computer readable medium having stored thereon computer executable code, when executed, causing a computer or a processor to perform the process of transitioning from a synchronous mode to an asynchronous mode in a medium access control (MAC) of a body area network (BAN), comprising:
setting a timer to a time period specified in a switch mode command for switching from the synchronous mode to the asynchronous mode within the BAN, upon receiving the switch mode command at a device;
upon expiration of the time period, tuning the device to a channel selected from a first set of channels in the BAN reserved for the asynchronous mode, wherein the first set of channels is different from a second set of channels that is reserved for the synchronous mode in the BAN; and
causing the device to operate in the asynchronous mode over the reserved channel, wherein the device is configured for asynchronously duty cycling between sleep and wakeup times.

8. A method for transitioning from an asynchronous mode to a synchronous mode in a medium access control (MAC) of a body area network (BAN) upon receiving a switch mode command, comprising:
setting a timer to a time period specified in the switch mode command for switching from the asynchronous mode to the synchronous mode within the BAN;
propagating the received switch mode command to other devices in the BAN;
upon expiration of the time period, tuning to a channel selected from a second set of channels in the BAN reserved for the synchronous mode, wherein the second set of channels is different from a first set of channels that is reserved for the asynchronous mode in the BAN; and
initializing a device to operate as either a master device or a slave device in the synchronous mode of operation, wherein the device is configured for synchronously duty cycling between sleep and wakeup times.

9. The method of claim 8, wherein the switch mode command includes at least a time when a mode switch is to be performed, the channel for the synchronous mode of operation, and identity of a group of devices that should switch their mode.

10. The method of claim 9, wherein the switch mode command is sent from either a peer device or an application layer.

11. The method of claim 10, further comprising checking by the device receiving the switch mode command if the device belongs to the group of devices designated in the switch mode command.

12. The method of claim 8, wherein each device initialized as a master device further performs:
scanning the channel reserved for the synchronous mode to detect at least global beacons transmitted by the at least one other master device;
joining an existing beacon group of the at least one other master device, when the channel is occupied by at least one other master device; and
transmitting global beacons on the channel by the master device switched to the synchronous mode, when the channel is not occupied by the at least one other master device.

13. The method of claim 8, further comprising, when each device is initialized as a slave device, scanning the channel reserved for the synchronous mode to detect at least local beacons transmitted by at least one master device; and joining the at least one master device when local beacons are detected on the channel.

14. The method of claim 13, further comprising checking by a master device if all its respective neighbor devices have switched to the synchronous mode; and switching back to the asynchronous mode during idle time to transmit the switch mode command from the master device to its respective neighbor devices when at least one neighbor device has not switched to the synchronous mode.

15. A non-transitory computer readable medium having stored thereon a computer executable code, when executed, causing a computer or a processor to perform the process of transitioning from an asynchronous mode to a synchronous mode in a medium access control (MAC) of a body area network (BAN), comprising:
  setting a timer to a time period specified in a switch mode command for switching from the asynchronous mode to the synchronous mode within the BAN, upon receiving the switch mode command at a device;
  propagating the received switch mode command to other devices in the BAN;
  upon expiration of the time period, tuning to a channel selected from a second set of channels in the BAN reserved for the synchronous mode, wherein the second set of channels is different from a first set of channels that is reserved for the asynchronous mode in the BAN; and
  initializing a device to operate as either a master device or a slave device in the synchronous mode of operation, wherein the device is configured for synchronously duty cycling.

16. A wireless device operable in a body area network, comprising:
  a radio transceiver configured to receive and transmit radio signals over a medium of the body area network;
  a processor;
  a memory for storing instructions that, when executed, configure the processor to:
    set a timer to a time period specified in a switch mode command for switching from the synchronous mode to the asynchronous mode within the BAN, upon receiving the switch mode command at the device;
    tune a device to a channel selected from a first set of channels in the BAN reserved for the asynchronous mode, upon expiration of the time period, wherein the first set of channels is different from a second set of channels that is reserved for the synchronous mode in the BAN; and
    cause the device to operate in the asynchronous mode over the reserved channel, wherein the device is configured for asynchronously duty cycling between sleep and wakeup times.

17. A wireless device operable in a body area network, comprising:
  a radio transceiver configured to receive and transmit radio signals over a medium of the body area network;
  a processor;
  a memory for storing instructions that, when executed, configure the processor to:
    set a timer to a time period specified in a switch mode command for switching from the asynchronous mode to the synchronous mode within the BAN, upon receiving the switch mode command at the device;
    propagate the received switch mode command to other devices in the BAN;
    tune to a channel selected from a second set of channels in the BAN reserved for the synchronous mode, upon expiration of the time period, wherein the second set of channels is different from a first set of channels that is reserved for the asynchronous mode in the BAN; and
    initialize a device to operate as either a master device or a slave device in the synchronous mode of operation, wherein the device is configured for synchronously duty cycling.

* * * * *